(12) United States Patent
Gellermann et al.

(10) Patent No.: US 6,205,354 B1
(45) Date of Patent: Mar. 20, 2001

(54) METHOD AND APPARATUS FOR NONINVASIVE MEASUREMENT OF CAROTENOIDS AND RELATED CHEMICAL SUBSTANCES IN BIOLOGICAL TISSUE

(75) Inventors: Werner Gellermann; Robert W. McClane; Nikita B. Katz; Paul S. Bernstein, all of Salt Lake City, UT (US)

(73) Assignee: University of Utah, Salt Lake City, UT (US)

( * ) Notice: Subject to any disclaimer, the term of this patent is extended or adjusted under 35 U.S.C. 154(b) by 0 days.

(21) Appl. No.: 09/335,932

(22) Filed: Jun. 18, 1999

(51) Int. Cl.[7] .................................................. A61B 6/00

(52) U.S. Cl. ............................................ 600/477; 356/301
(58) Field of Search .................................. 600/473, 476, 600/475, 477, 310, 318; 356/301, 303; 606/2–4, 10

(56) References Cited

U.S. PATENT DOCUMENTS

| | | |
|---|---|---|
| 3,563,233 | 2/1971 | Bodine . |
| 4,144,464 | 3/1979 | Loree et al. ........................ 307/88.3 |
| 4,318,057 | 3/1982 | Buchwald et al. ..................... 372/70 |
| 4,500,995 | 2/1985 | White ....................................... 372/3 |
| 4,519,400 | 5/1985 | Brenman et al. . |
| 4,665,921 | 5/1987 | Teranish et al. . |
| 4,758,081 | 7/1988 | Barnes ................................. 351/221 |
| 4,807,240 | 2/1989 | Goldstone ............................. 372/69 |

(List continued on next page.)

FOREIGN PATENT DOCUMENTS

| | | |
|---|---|---|
| 0 722 692 A1 | 7/1996 | (EP) . |
| WO 92/10131 | 6/1992 | (WO) . |
| WO 92/15008 | 9/1992 | (WO) . |

OTHER PUBLICATIONS

Tom C. Bakker Schut; Gerwin J. Puppels; Yvonne M. Kraan; Jan Greve; Louis L.J. Van Der Maas; and, Carl G. Figdor, "Intracellular Carotenoids Levels Measured by Raman Microspectroscopy: Comparison of Lymphocytes from Lung Cancer Patients and Healthy Individuals," Int. J. Cancer (Pred. Oncol.): 74,20–25 (1997).

Monika Gniadecka; Hans C. Wulf; Ole F. Nielsen; Daniel H. Christensen; and, Jana Hercogova, "Distinctive Molecular Abnormalities in Benign and Malignant Skin Lesions: Studies by Raman Spectroscopy," Photochemistry and Photobiology, 1997, 66(4): 418–423.

Christopher J. Frank; Douglas C.B. Redd; Ted S. Gansler; and, Richard L. McCreery, "Characterization of Human Breast Biopsy Specimens with Near–IR Raman Spectroscopy," Anal. Chem. 1994, 66, 319–326.

Primary Examiner—Brian L. Casler
(74) Attorney, Agent, or Firm—Workman, Nydegger & Seeley

(57) ABSTRACT

A method and apparatus are provided for the determination of levels of carotenoids and similar chemical compounds in biological tissue such as living skin. The method and apparatus provide a noninvasive, rapid, accurate, and safe determination of carotenoid levels which in turn can provide diagnostic information regarding cancer risk, or can be a marker for conditions where carotenoids or other antioxidant compounds may provide diagnostic information. Such early diagnostic information allows for the possibility of preventative intervention. The method and apparatus utilize the technique of resonance Raman spectroscopy to measure the levels of carotenoids and similar substances in tissue. In this technique, laser light is directed upon the area of tissue which is of interest. A small fraction of the scattered light is scattered inelastically, producing the carotenoid Raman signal which is at a different frequency than the incident laser light, and the Raman signal is collected, filtered, and measured. The resulting Raman signal can be analyzed such that the background fluorescence signal is subtracted and the results displayed and compared with known calibration standards.

32 Claims, 7 Drawing Sheets

U.S. PATENT DOCUMENTS

| | | | |
|---|---|---|---|
| 4,832,483 | 5/1989 | Verma | 356/39 |
| 4,852,579 | 8/1989 | Gilstad et al. | 128/665 |
| 4,858,238 | 8/1989 | Cardimona | 372/3 |
| 4,969,868 | 11/1990 | Wang . | |
| 5,034,228 | 7/1991 | Meybeck et al. | 424/401 |
| 5,124,313 | 6/1992 | Schaeffer et al. | 514/2 |
| 5,275,168 | 1/1994 | Reintjes et al. | 128/665 |
| 5,290,605 | 3/1994 | Shapira | 424/439 |
| 5,303,026 | 4/1994 | Strobl et al. | 356/318 |
| 5,304,170 | 4/1994 | Green | 606/9 |
| 5,346,488 | 9/1994 | Prince et al. | 606/7 |
| 5,418,797 | 5/1995 | Bashkansky et al. | 372/3 |
| 5,421,337 | 6/1995 | Richards-Kortum et al. | 128/665 |
| 5,432,610 | 7/1995 | King et al. | 356/432 |
| 5,451,785 | 9/1995 | Faris | 250/330 |
| 5,452,723 | 9/1995 | Wu et al. | 128/664 |
| 5,553,616 | 9/1996 | Ham et al. | 128/633 |
| 5,556,612 | 9/1996 | Anderson et al. | 424/59 |
| 5,567,628 | 10/1996 | Tarcha et al. | 436/525 |
| 5,579,773 | 12/1996 | Vo-Dinh et al. | 128/665 |
| 5,590,660 | 1/1997 | MacAulay et al. | 128/664 |
| 5,643,623 | 7/1997 | Schmitz et al. | 426/73 |
| 5,657,754 | 8/1997 | Rosencwaig | 128/633 |
| 5,697,373 | 12/1997 | Richards-Kortum et al. | 128/664 |
| 5,733,507 | 3/1998 | Zakim | 422/101 |
| 5,873,831 | 2/1999 | Bernstein et al. | 600/473 |

METHOD AND APPARATUS FOR NONINVASIVE MEASUREMENT OF CAROTENOIDS AND RELATED CHEMICAL SUBSTANCES IN BIOLOGICAL TISSUE

BACKGROUND OF THE INVENTION

1. The Field of the Invention

The present invention relates generally to techniques for measuring levels of chemical compounds found in biological tissue. More specifically, the invention relates to a method and apparatus for the noninvasive detection and measurement of levels of carotenoids and related chemical substances in biological tissue, which can be used as a diagnostic aid in assessing antioxidant status and detecting malignancy diseases or risk thereof.

2. The Relevant Technology

Carotenoids are plant pigments available from the diet which have important functions in the human body. The role of carotenoids in human health is a rapidly expanding area of research. Much carotenoid research has focused on their role as precursors to retinoids or vitamin A, but current research is also being conducted on other functions of carotenoids. These include antioxidant activities, modulation of the immune response, cell-to-cell communication and gap junction modulation.

It has been demonstrated that carotenoids offer some degree of biologic protection against the formation of malignancies in various tissues. For example, carotenoids have been shown in animal models to prevent carcinoma formation in tissues such as skin, salivary gland, mammary gland, liver, and colon. In addition, low levels of carotenoids and related substances such as retinoids have been assessed as high risk factors for malignant lesions. For example, having low levels of the carotenoid lycopene has been associated with prostate and cervical cancer; the carotenoids lutein, zeaxanthin, alpha-carotene, and beta-carotene with lung cancer; and beta-carotene with oral cancer. Therefore, quantitatively measuring the chemical concentrations of these carotenoids, retinoids and other related substances provides an indicator of the risk or presence of cancer.

The most common cancer in the United States is skin cancer. Despite attempts at patient education, skin cancer rates continue to rise. Methods to provide detection of the levels of chemicals which are associated with skin related malignancies are of great assistance to physicians and medical personnel in the early diagnosis and treatment of skin cancer.

It has been theorized that carotenoids in the skin provide biologic protection from cutaneous malignancy. Most findings, however, have been somewhat compromised by the fact that concentrations of carotenoids in skin and skin malignancies were never measured directly, with data on levels of carotenoids in patients being derived only indirectly from blood plasma.

Prior methods used to detect the presence of chemicals associated with skin cancer have mainly been through the analysis of tissues obtained by biopsies or other invasive procedures. The standard method presently used for measuring carotenoids is through high-performance liquid chromatography (HPLC) techniques. Such techniques require that large amounts of tissue sample be removed from the patient for subsequent analysis and processing, which typically takes at least twenty four hours to complete. In the course of these types of analyses, the tissue is damaged, if not completely destroyed. Therefore, a noninvasive and more rapid technique for measurement is preferred.

A noninvasive method for the measurement of carotenoid levels in the macular tissue of the eye is described in U.S. Pat. No. 5,873,831, the disclosure of which is herein incorporated by reference, in which levels of carotenoids and related substances are measured by a technique known as Raman spectroscopy. This is a technique which can identify the presence and concentration (provided proper calibration is performed) of certain chemical compounds. In this technique, nearly monochromatic light is incident upon the sample to be measured, and the inelastically scattered light which is of a different frequency than the incident light is detected and measured. The frequency shift between the incident and scattered light is known as the Raman shift, and the shift corresponds to an energy which is the "fingerprint" of the vibrational or rotational energy state of certain molecules. Typically, a molecule exhibits several characteristic Raman active vibrational or rotational energy states, and the measurement of the molecule's Raman spectrum thus provides a fingerprint of the molecule, i.e., it provides a molecule-specific series of spectrally sharp vibration or rotation peaks. The intensity of the Raman scattered light corresponds directly to the concentration of the molecule(s) of interest.

One difficulty associated with Raman spectroscopy is the very low signal intensity which is inherent to Raman scattered light. It is well known that the scattered light intensity scales with the frequency raised to the fourth power. The weak Raman signal must be distinguished from Rayleigh scattered light, which is elastically scattered light of the same frequency as the incident light and which constitutes a much greater fraction of the total scattered light. The Raman signal can be separated from Rayleigh scattered light through the use of filters, gratings, or other wavelength separation devices; however, this can have the effect of further weakening the measured Raman signal through the additional attenuation which can occur when the light passes through a wavelength separation device. In practice, the Raman scattered light is extremely difficult to detect. One might attempt to increase the Raman signal by increasing the incident laser power on the tissue sample, but this can cause burning or degradation of the sample.

In order to overcome some of these difficulties, a technique known as resonance Raman spectroscopy has been used, as described in U.S. Pat. No. 5,873,831, referenced hereinabove. Such a technique is also described in U.S. Pat. No. 4,832,483, the disclosure of which is herein incorporated by reference. In resonance Raman spectroscopy, the incident illumination utilized has a frequency which corresponds to the resonance frequency corresponding to electronic energy transitions of the molecules of interest. This has the effect of strongly enhancing the Raman output signal without using a higher intensity input signal, thereby avoiding damage to the sample which can be caused by laser burning. Also, these resonance Raman signals have much higher intensity than off-resonance Raman signals which are virtually invisible. Therefore, in resonance Raman spectroscopy only those Raman signals which belong to the species of interest are obtained.

In the above referenced U.S. Pat. No. 5,873,831, the resonance Raman technique is used to measure the levels of the carotenoids lutein and zeaxanthin, two chemicals which are associated with healthy macular tissue of the human eye. The above referenced U.S. Pat. No. 4,832,483 uses resonance Raman spectroscopy to measure certain carotenoids in blood plasma, and suggests the use of the ratios of the intensities of the Raman spectral peaks as a method of indicating the presence of various malignancy diseases.

Yet another difficulty associated with Raman measurements is that the substances of interest in the skin not only scatter incident light, but can absorb and subsequently fluoresce with substantial intensity. This fluorescence often comprises a very strong, broad signal which tends to "drown out" or overwhelm the Raman spectral peaks, thereby making identification and quantification of the substances of interest practically impossible.

Fluorescence spectroscopy is itself another technique which can be used to measure amounts of chemical compounds in biological tissue. For example, U.S. Pat. No. 5,697,373 discloses use of fluorescence and/or Raman spectroscopy to detect tissue abnormality in the cervix. The disadvantage of fluorescence measurements is that since many different molecules fluoresce in broad bands of frequencies, such measurements cannot be used to conclusively identify the presence or concentration of a particular substance.

It would therefore be a significant advance to provide a method and apparatus for the safe, noninvasive, rapid, accurate, and specific measurement of the levels of carotenoids and other similar chemical compounds which are present in varying degrees in biological tissues, and to use this information to aid in the assessment of cancer risk or disease risk in all types of biological tissue.

SUMMARY AND OBJECTS OF THE INVENTION

It is a primary object of the present invention to provide a method and apparatus for rapid, noninvasive, and quantitative measurement of the levels of carotenoids and related chemical substances in biological tissues. It is yet another object of the present invention to utilize the information obtained from such measurements to assess the risk of malignancy disease such as skin cancer.

Yet another object of the present invention is to provide a method and apparatus for the safe measurement of the levels of carotenoids and related substances in biological tissue in vivo which decreases the time and expense required by conventional methods.

Additional objects and advantages of the invention will be set forth in the description which follows, or may be learned by the practice of the invention.

To achieve the foregoing objects, and in accordance with the invention as embodied and broadly described herein, a method and apparatus for the measurement of the levels of carotenoids and other related substances in biological tissue such as living skin is provided. In particular, the method of the present invention provides a noninvasive, rapid, safe, and accurate determination of the levels of carotenoids and similar substances in tissue, which in turn can be used to provide diagnostic information regarding cancer risk such as for skin cancer and skin related malignancies, or can be a marker for conditions where carotenoids or other antioxidant compounds may provide diagnostic information. Such early diagnostic information allows for the possibility of preventative intervention.

The present invention uses the technique of resonance Raman spectroscopy to quantitatively measure the levels of carotenoids and similar substances in tissue such as skin. In this technique, monochromatic laser light is directed upon the area of tissue which is of interest. The scattered light from the tissue includes a main portion of Rayleigh scattered light, which is of the same frequency as the incident laser light. A small fraction of the scattered light is scattered inelastically at different frequencies than the incident laser light, which is the Raman signal. The Rayleigh and the Raman scattered light are separated, typically by wavelength selective filtering, and the resulting Raman signal is measured using a sensitive light detection system. The resulting Raman signal can be analyzed by a data quantifing system wherein the background fluorescence signal is subtracted and the results displayed and compared with known calibration standards.

These and other objects and features of the present invention will become more fully apparent from the following description, or may be learned by the practice of the invention as set forth hereinafter.

BRIEF DESCRIPTION OF THE DRAWINGS

In order to illustrate the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting in scope, the invention will be described and explained with additional specificity and detail through the use of the accompanying drawings in which.

DETAILED DESCRIPTION OF THE INVENTION

Figure 1:
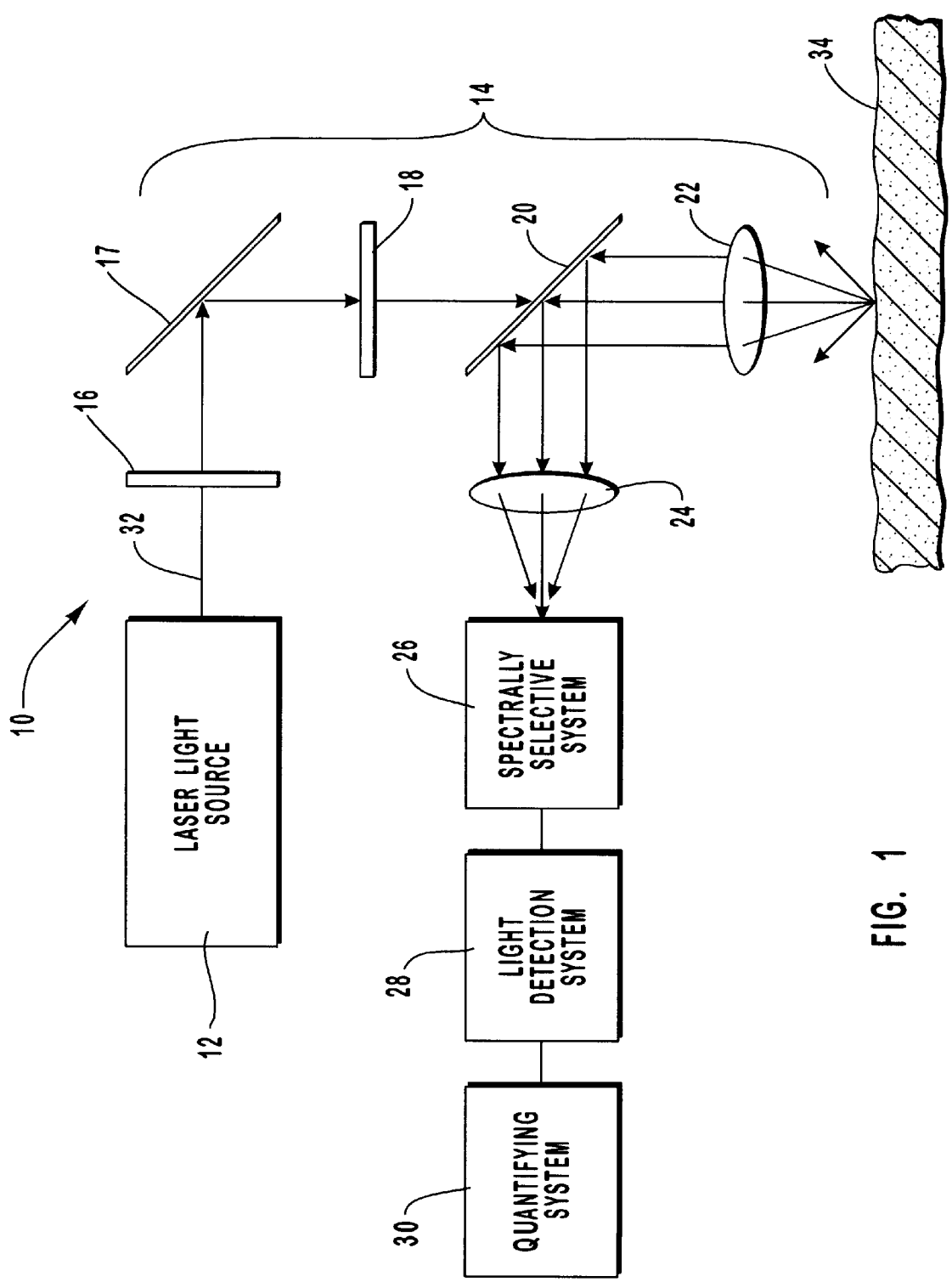
FIG. 1 is a general schematic depiction of the apparatus according to the present invention.

The present invention is directed to a method and apparatus for the noninvasive detection and measurement of carotenoids and related chemical substances in biological tissue as well as in bodily fluids. In particular, the present method and apparatus make possible the rapid, noninvasive, and quantitative measurement of the concentration of carotenoids, as well as their isomers and metabolites, in biological tissues such as human skin. This is accomplished without the requirement of removing tissue or preparing samples for HPLC analysis, as required in prior techniques.

The invention can be used in a direct and quantitative optical diagnostic technique, which uses low intensity illumination of intact tissue and provides high spatial resolution, allowing for precise quantification of the carotenoid levels in the tissue. Such a diagnostic technique can aid in the detection of tissue abnormalities such as malignancy diseases.

Examples of biological tissues which can be measured noninvasively with the technique of the invention include human skin, cervix, colon, and lungs. Examples of bodily fluids that can be measured include saliva, whole blood, and mucus.

The present invention employs the technique of resonance Raman spectroscopy, which is used to identify and quantify the presence of carotenoids and similar substances in biological tissue such as the skin. In this technique, nearly monochromatic laser light is directed onto the tissue and the scattered light is then spectrally filtered and detected. The scattered light comprises both Rayleigh and Raman scattered light. The Rayleigh light is light which is elastically scattered, which means it is scattered at the same wavelength as the incident laser light. Most of the scattered light is scattered elastically. A small remainder of the light is scattered in an inelastic fashion, and is therefore of different frequencies than the incident laser light. This inelastically scattered light forms the Raman signal. The frequency difference between the laser light and the Raman scattered light is known as the Raman shift and is typically measured as a difference in wave numbers (or difference in frequencies or wavelengths). The magnitude of the Raman shifts is an indication of the type of chemical present, and the intensities of the Raman signal peaks correspond directly to the chemical concentration. One of the reasons why Raman spectroscopy is so useful is that specific wave number shifts correspond to certain modes of vibrational or rotational of these chemical structures. The Raman shift is independent of the wavelength of incident light used, and hence, in theory, any strong and fairly monochromatic light source can be used in this technique.

The technique of resonance Raman spectroscopy used in the present invention aids in overcoming the difficulties associated with measuring the inherently weak Raman signal. In resonance Raman spectroscopy, a laser source of wavelength near the absorption peaks corresponding to electronic transitions of the molecules of interest is utilized. By making the incident light close to resonant with the electronic absorption frequencies of the molecules of interest, the Raman signal is substantially enhanced, which provides the advantage of being able to use lower incident laser power (which in turn minimizes tissue damage) and also results in less stringent requirements for the sensitivity of the detection equipment.

Raman spectroscopy in tissues using short visible laser wavelengths normally would be impossible due to high native fluorescence, particularly in skin tissue, which masks the weaker Raman signals. The present invention uses short visible wavelengths in a way which selectively and drastically increases the carotenoid Raman signal due to selective resonance coupling of the laser with this family of molecules, which themselves are known to exhibit only very weak fluorescence. This signal enhancement allows carotenoid levels to be determined even in the presence of the strong native fluorescence. Since the tissue not only scatters the light (elastically and inelastically), but also absorbs the light, background fluorescence is produced during Raman spectroscopy measurements. As discussed in further detail below, the background fluorescence can be subtracted from the Raman spectrum and the resulting spectrum can be expanded to give a clear indication of the Raman carotenoid signals. It is unexpected that a useful Raman signal can be measured at the low laser power levels in the visible wavelength range utilized in the present invention as normally the Raman signal would be buried in the typically high fluorescence background of human tissue.

In a method for the noninvasive measurement of carotenoids and related chemical substances in biological tissue according to the present invention, a light source such as a laser is utilized which generates light at a wavelength that produces a Raman response with a wavelength shift for the carotenoids to be detected. The laser light is directed onto the tissue, with the light having an intensity which does not cause destruction of the tissue and does not substantially alter carotenoid levels. The elastically and inelastically scattered light from the tissue is collected, with the inelastically scattered light having characteristic energy shifts and quantifiable intensities which produce a Raman signal corresponding to carotenoids in the tissue. The elastically scattered light is filtered, and the intensity of the inelastically scattered light forming the Raman signal is quantified.

The intensity of the light scattered inelastically from the carotenoid molecules and forming the Raman signal can be compared with the intensity of Raman scattering from normal biological tissue to assess the risk or presence of a malignancy disease such as cancer in a live subject. For example, a substantial difference between the intensity of the Raman signal of suspected malignant biological tissue and the intensity of Raman scattering from adjacent normal biological tissue indicates the presence or risk of disease. The intensity of the Raman signal can also be quantified to assess the antioxidant status of the tissue.

FIG. 1 is a general schematic depiction of the apparatus of the present invention, generally labeled 10, for measuring carotenoids and like substances in biological tissue using Raman spectroscopy. The apparatus 10 includes a coherent light source 12, which in one preferred embodiment is a low power argon ion laser. Alternatively, light source 12 may comprise other devices for generating nearly monochromatic light. The light source 12 generates light in a wavelength which overlaps the absorption bands of the carotenoids to be detected. Preferably, in the case of carotenoids, light source 12 generates laser light in a range from about 450 nm to about 520 nm, which corresponds to the absorption band of the carotenoids of interest. Such laser light is readily available from commercially produced argon lasers. For example, blue/green argon laser lines can be used to resonantly excite the electronic absorption of the carotenoids, such as the 4880 Å or 5145 Å lines of an argon laser. It should be understood, however, that the present invention is not limited to light generated within these wavelengths, since other wavelengths of light could be used if desired, e.g, UV laser lines overlapping the absorption transitions of carotenoids occurring in the ultraviolet spectral region.

The light source 12 is in optical communication with a light beam delivery and collection system 14 which can include various optical components for directing laser light to the tissue to be measured and collecting the scattered light. As shown in FIG. 1, the optical components of delivery and collection system 14 include a neutral density filter 16, a diffraction grating 17, a slit 18, a beam splitter 20, a first lens 22, and a second lens 24. The interaction of these optical components with a laser beam from light source 12 will be discussed in further detail below.

The delivery and collection system 14 is in optical communication with a spectrally selective system 26 such as a Raman spectrometer, which performs the function of spectral separation of the Raman scattered light from Rayleigh scattered light. The spectrally selective system 26 can include various optical components such as grating monochromators, holographic filters, dielectric filters, acousto-optic filters, prisms, combinations thereof, and the like.

The spectrally selective system 26 is in optical communication with a detection means such as a light detection system 28, which is capable of measuring the intensity of the Raman scattered light as a function of frequency in the frequency range of interest such as the frequencies characteristic of carotenoids in the skin. The light detection system 28 may comprise, but is not limited to, devices such as a CCD (Charge Coupled Device) detector array, an intensified CCD detector array, a photomultiplier apparatus, photodiodes, or the like.

The spectrally selective system 26 and light detection system 28 can be selected from commercial spectrometer systems such as a medium-resolution grating spectrometer employing rapid detection with a cooled charge-coupled silicon detector array. For example, a monochromator can be used which employs a dispersion grating with 1200 lines/mm, and a liquid nitrogen cooled silicon CCD detector array with a 25 $\mu$m pixel width. Another suitable spectrometer is a holographic imaging spectrometer, which is interfaced with a CCD camera and employs a volume holographic transmission grating. The spectrally selective system 26 and light detection system 28 can also be combined into a Raman imaging system that includes spectrally selective optical elements used in association with a low light level CCD imaging array such as an intensified CCD camera.

The detected light is preferably converted by light detection system 28 into a signal which can be visually displayed on an output display such as a computer monitor or the like. It should be understood that the light detection system 28 may also convert the light signal into other digital or numerical formats, if desired. The resultant Raman signal intensities are preferably analyzed via a quantifying means such as a quantifying system 30, which may be calibrated by comparison with chemically measured carotenoid levels from other experiments. The quantifying system 30 may be a computer, preferably one in which data acquisition software is installed that is capable of spectral manipulations, such as subtraction of the background fluorescence spectrum, thereby allowing for a background-free Raman signal while using safe laser power densities. The quantifying system 30 may also comprise a CCD image display or monitor. The quantifying system 30 may be combined with the output display in one computer and can calibrate the results with carotenoid levels obtained from other experiments such that the signal intensity is calibrated with actual carotenoid levels.

During operation of apparatus 10, a laser beam 32 is generated from light source 12 and is directed through an input optical fiber to delivery and collection system 14. The laser beam 32 is directed through neutral density filter 16 which reduces the laser power, and is reflected off of diffraction grating 17 and passed through slit 18 to eliminate laser plasma lines. The beam is then directed through beam splitter 20 and weakly focused by first lens 22 onto a tissue 34 to be measured. The power density or light intensity of the beam is preferably in a range up to about 200 mW/cm$^2$ at an exposure time of about 1 ms to about 10,000 s. The backscattered light from tissue 34 is then collected by first lens 22 and reflected offofbeam splitter 20 toward second lens 24, which focuses the light into an output optical fiber for routing the light to spectrally selective system 26 such as a Raman spectrometer. After the Raman signal has been separated from the Rayleigh light in spectrally selective system 26, the Raman signal is directed to light detection system 28, which measures the light intensity as a function of frequency in the range covering the Raman peaks of interest, approximately 800 to 2000 cm$^{-1}$ for carotenoids. The light detection system 28 then converts the Raman signal into a form suitable for visual display such as on a computer monitor or the like, and the resultant Raman signal is analyzed via quantifying system 30.

The present invention is particularly useful in the detection of total carotenoid content in human skin. Several of the carotenoids which have been found to be associated with healthy skin include all-trans-$\beta$-carotene, lycopene, $\alpha$-carotene, $\gamma$-carotene, phytoene, phytofluene, septapreno-$\beta$-carotene, 7,7' dihydro-$\beta$-carotene, astaxanthin, canthaxanthin, zeaxanthin, lutein, $\beta$-apo-8'-carotenal, violaxanthin, and rhodoxanthin. These are chain-like molecules with different lengths and attachments, all having a carbon backbone with alternating carbon double and single bonds, respectively. The vibration of these bonds, common to all carotenoids, can be detected with Raman spectroscopy. It is known from separate measurements that the wavenumber shifts of these carotenoids are generally in the range from 800 to 2000 cm$^{-1}$ (wavenumbers). For example, the carotenoids lutein and zeaxanthin are known to have wavenumber shifts of approximately 1160 cm$^{-1}$ and 1520 cm$^{-1}$, respectively.

Carotenoids are an important component of the skin's antioxidant defense systems, where they are thought to act as free radical and singlet oxygen scavengers. Furthermore, carotenoids protect the skin from a number of harmful reactive oxygen species (ROS), which are formed, for example, by excessive exposure of skin to ultra-violet (UV) light such as from sunlight. The ROS can potentially cause oxidative cell damage and the formation of skin cancers such as basal cell carcinoma, squamous cell carcinoma, and malignant melanoma. In addition, UV light exposure can lead to immuno-suppression and premature skin aging. Once formed, the ROS efficiently react with DNA, proteins, and unsaturated fatty acids, causing DNA strand breaks and oxidative damage, as well as protein-protein and protein-DNA cross links. Oxidation of lipids can result in the formation of lipid peroxides which persist a relatively long time in the cells and can thus initiate radical chain reactions and enhance oxidation damage.

It has been previously demonstrated that there is a correlation between the levels of carotenoids, retinoids, and similar chemical substances in the skin and the risk of skin cancer and other skin disorders. People with low levels of carotenoids in their skin are at a significantly greater risk of getting skin cancer. Therefore, if a determination can be made of the levels of carotenoids which are present in the skin, the risk for cancer can be assessed; and if low levels of carotenoids are measured, preventative steps can be taken, such as dietary supplements.

Current methods for evaluating the presence of skin cancer generally include excising an area of the suspected tissue and performing a histological analysis. This is an invasive procedure and is usually performed in the later stage of cancer, and thus is not useful in early detection of cancer or precancerous conditions in an efficient and timely manner in order to provide proper treatment. The present invention overcomes these difficulties by providing for early noninvasive measurement of carotenoids to aid in the determination of cancer risk.

The present invention not only provides for a rapid, non-invasive assessment of carotenoid levels in a variety of human tissues and bodily fluids, but also has many additional beneficial uses. These include assessing the overall antioxidant status in human tissue; providing for early cancer detection using spatially resolved Raman data or Raman images; providing a screening tool suitable for use in large population studies of cancer prevention and other diseases involving carotenoids or other antioxidants; providing for monitoring of dietary manipulation of tissue carotenoid or other antioxidant content; and providing a tool to assess carotenoid distribution and uptake from cosmetic compounds.

The methods and apparatus of the invention are especially effective in measuring the carotenoid levels in skin, skin lesions, and skin malignancies. The present invention allows two-dimensional Raman mapping to be developed which will provide a non-invasive method for defining tumor margins, thus eliminating time consuming and tedious sections and allowing for instant intraoperative tumor margin delineation. The measurement of carotenoid levels can also be used as a predictor of malignant potential of individual cutaneous lesions.

Various experiments were performed which demonstrate that strong Raman signals are readily obtainable for various areas of living human skin using low light exposures. The following examples set forth the apparatus and procedures utilized in these experiments as well as the results derived therefrom.

EXAMPLE 1

Figure 2:
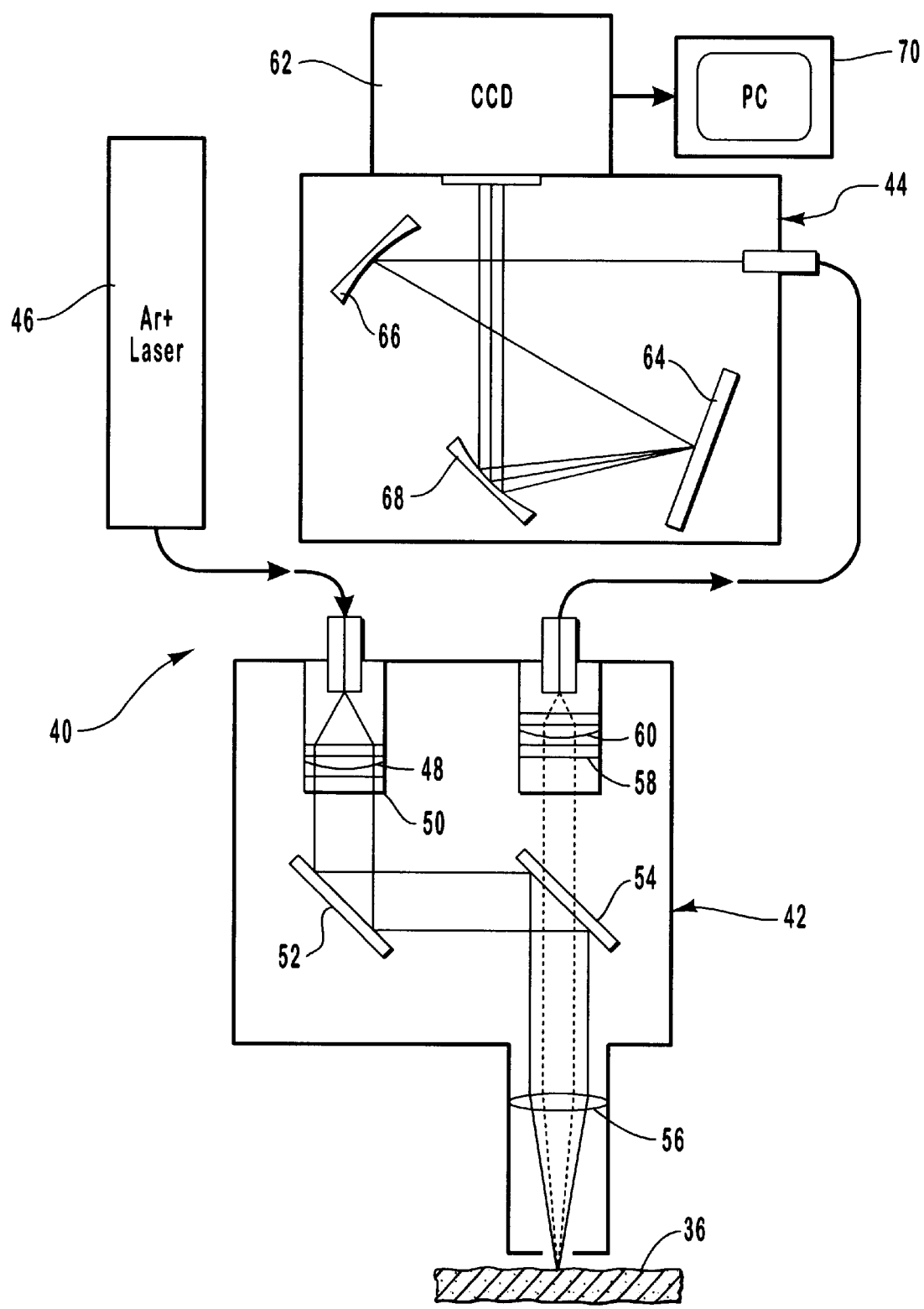
FIG. 2 is a schematic depiction of an experimental apparatus according to the present invention.

An experimental apparatus 40 suitable for Raman measurements of carotenoids in human skin was assembled as shown schematically in FIG. 2. The apparatus 40 includes a light module 42 which contains the light beam delivery and collection optics, and a Raman module 44 which contains the spectrometer components. The light module 42 is designed as a hand-held beam delivery and collection device, and can be placed in close proximity to the scattering sample (e.g, human skin) such that the sample is within about 5 cm of the light collecting optics. This results in an apparatus with a high f-number and hence high light throughput.

As excitation source, the blue/green lines of an argon laser 46 were used. The argon laser 46 is in optical communication with light module 42 such that the excitation laser light is routed through an input optical fiber into light module 42 during operation. A portion of the laser light is split off by a beam splitter and sampled with a photodetector for reference purposes (not shown) prior to entering light module 42. The laser light is coupled out of the input optical fiber and into light module 42 where it is collimated with a first lens 48 and passed through a first narrow bandwidth filter 50 (e.g, dielectric interference filter or holographic notch filter). The light is then reflected off of a pair of dichroic beam splitters 52 and 54, and is directed onto living skin tissue 36 via a second lens 56. The narrow bandwidth filter 50 serves to remove laser plasma lines, potential fiber emission and fiber Raman scattering. The beam splitters 52 and 54 are dielectric and coated to pass wavelengths of 488 nm and simultaneously reflect wavelengths larger than about 500 nm. The laser spot size on the skin tissue can be manipulated by proper choice of the focal length of lens 56. In the present experiments, a skin spot size of about 2 mm was illuminated with laser light of about 200 mW/cm$^2$ power density (which is considered safe by ANSI standards).

The Raman shifted signals from the skin tissue are collected in a 180 degree backscattering geometry. The scattered light is collected and collimated by lens 56 and routed towards an output optical fiber leading to Raman module 44, via beam splitter 54, a second narrow bandwidth filter 58, and a third lens 60. The filter 58 is designed to reject the Rayleigh component of the Raman scattered light and to simultaneously transmit the carotenoid Stokes signals with high light throughput.

The Raman module 44 is a commercially available grating spectrometer, and is interfaced to a CCD camera 62 with a silicon detector array. The Raman scattered light from light module 42 is coupled out of the output optical fiber and sent to a reflection grating 64 via a first mirror 66. The light is reflected from reflection grating 64 as wavelength dispersed signals and imaged onto the detector array of CCD camera 62 via a second mirror 68. Besides employing a single grating stage for light dispersion and thus allowing for high light throughput, the Raman module 44 is the size of a shoe-box and therefore compact, movable and suitable for use on human subjects. The CCD camera 62 is operatively connected with a personal computer 70 such that the signals imaged on the detector array are displayed on a monitor of computer 70.

EXAMPLE 2

Figure 3:
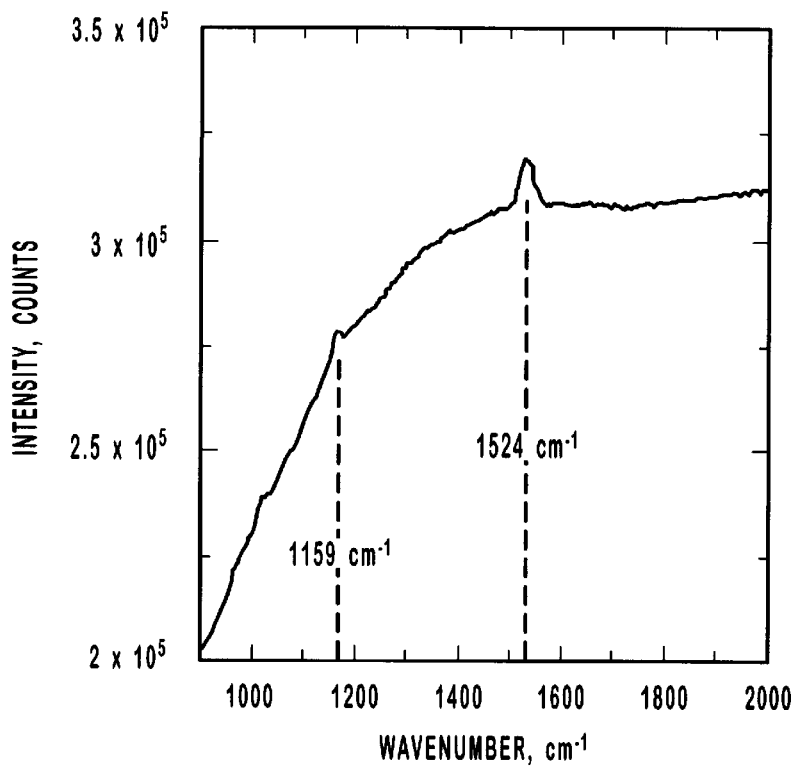
FIG. 3 is a graph showing the Raman spectra obtained from living skin together with the background fluorescence spectra.
Figure 4:
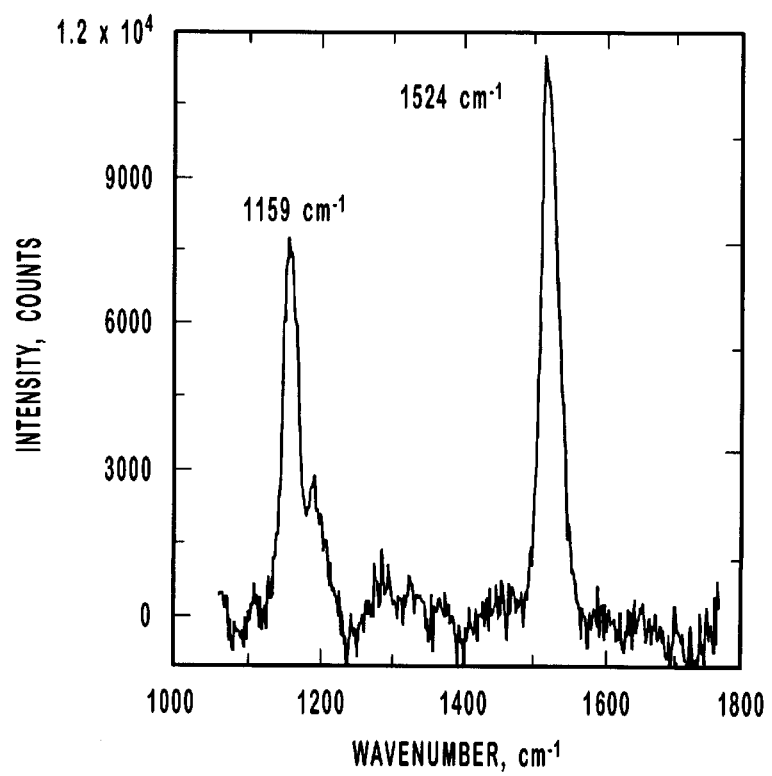
FIG. 4 is a graph showing the Raman spectra of FIG. 3 after the background fluorescence has been subtracted.

A typical Raman carotenoid spectrum obtained from the skin of a healthy human volunteer with the apparatus of Example 1 is shown in the graph of FIG. 3. A skin spot size of about 2 mm was illuminated with laser light at 488 nm with 10 mW power. The data was plotted in the standard format of photon count (intensity) vs. wavenumber shift. The spectrum was measured using resonance Raman techniques for further enhancement of the inherently weak Raman signal. Raman peaks characteristic of carotenoid molecules appear in the graph of FIG. 3, which are superimposed on a broad fluorescence background. Nevertheless, the Raman peaks are clearly resolved, and, using the high dynamic sensitivity range of the CCD detector, can be displayed with good sensitivity resolution and high signal-to-noise ratio. This is shown for example in FIG. 4, where the fluorescence background has been fitted with a higher order polynomial and subtracted from the spectrum. The background fluorescence spectrum can be subtracted by commercially available spectral acquisition software (e.g., Kestrel Spec, available from Rhea Corp). The two peaks correspond to the 1159 and 1524 cm$^{-1}$ carbon-carbon single and double bond stretching vibrations, respectively, of the carotenoid molecules, and their peak heights correlate with existing carotenoid concentrations in the skin.

EXAMPLE 3

Figure 5:
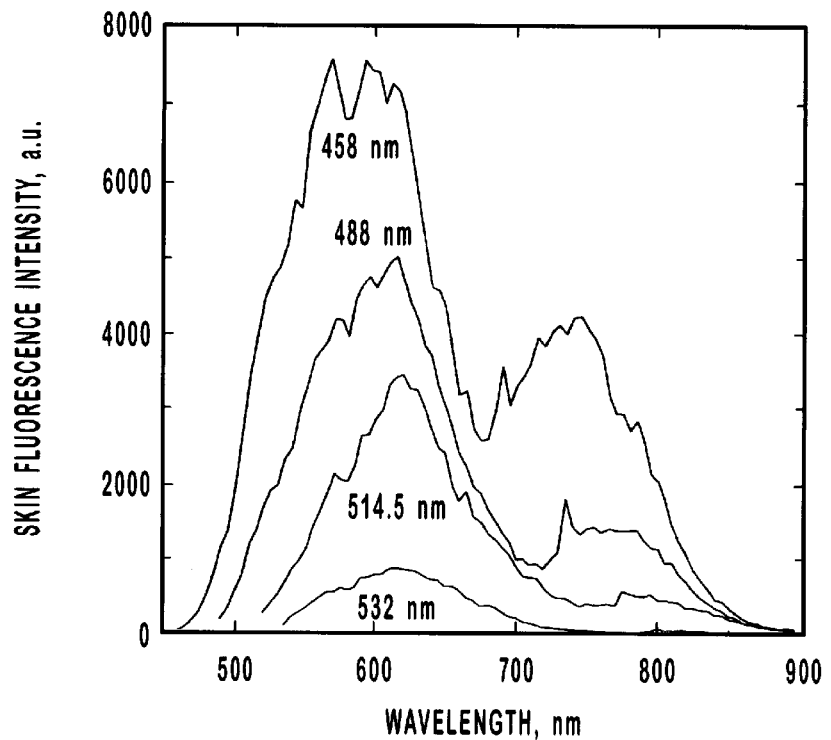
FIG. 5 is a graph showing the fluorescence background of human skin measured at various laser excitation wavelengths.
Figure 6:
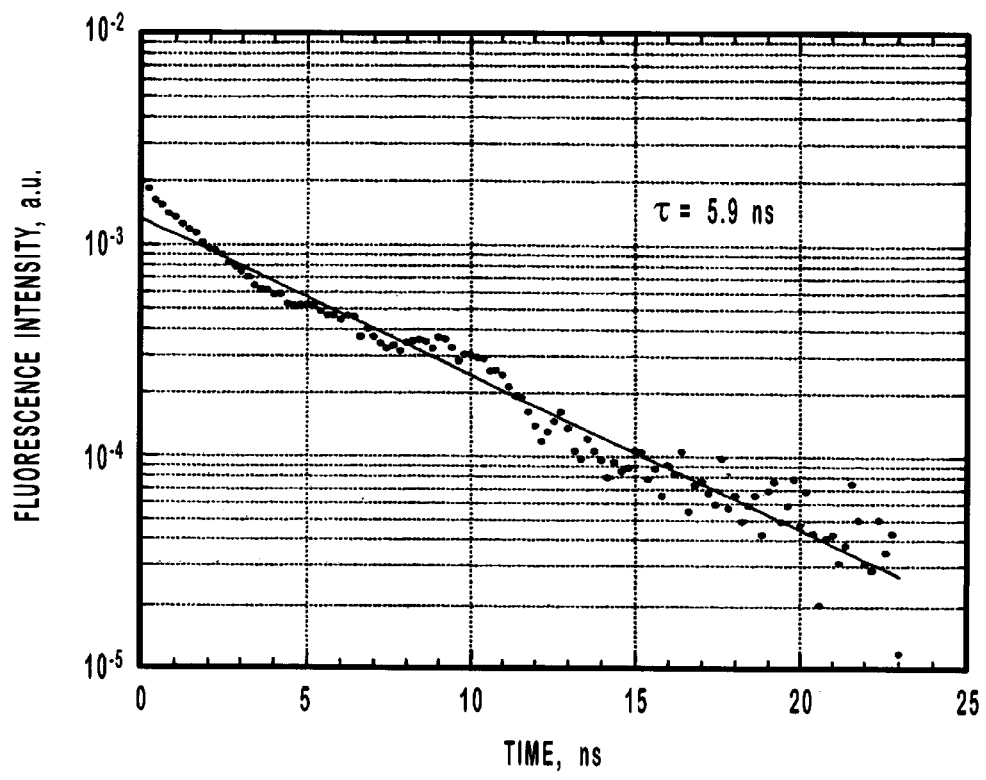
FIG. 6 is a graph showing the decay kinetics of human skin fluorescence.

In order to further characterize the fluorescence background and its influence on the Raman measurements of human skin, the fluorescence emission spectra of human skin was measured in vivo for blue/green laser excitation wavelengths of 458 nm, 488 nm, 514.5 nm, and 532 nm. The power density of the laser was 0.2 W/cm$^2$, and the sampling time per 1 nm wavelength interval was 1 second. The results are shown in the graph of FIG. 5, revealing that the emission consists of at least two broad and overlapping bands, one centered near 600 nm, and the other near 750 nm. With increasing excitation wavelengths, the emission central maxima shift slightly to longer wavelengths, their overall intensities decrease, and at 532 nm excitation only the short wavelength component of the emission is left. The origin of this so called skin "autofluorescence" is due to intrinsic fluorophores, i.e. collagen cells, porphyrin molecules, etc., and not due to carotenoid emission. This conclusion is further supported by the decay kinetics of the fluorescence, shown in the graph of FIG. 6. This graph plots the fluorescence intensity at ~600 nm as a function of time after excitation with short (100 ps) pulses from a mode-locked laser at 532 nm. Plotted on a semi-logarithmic scale, the intensity is seen to decay almost singly-exponentially with a lifetime of ~6 ns. This value is typical for the spontaneous emission lifetime of native fluorophores present in the skin, and is orders of magnitude larger than the lifetime reported for carotenoids (~200 fs).

EXAMPLE 4

Figure 7:
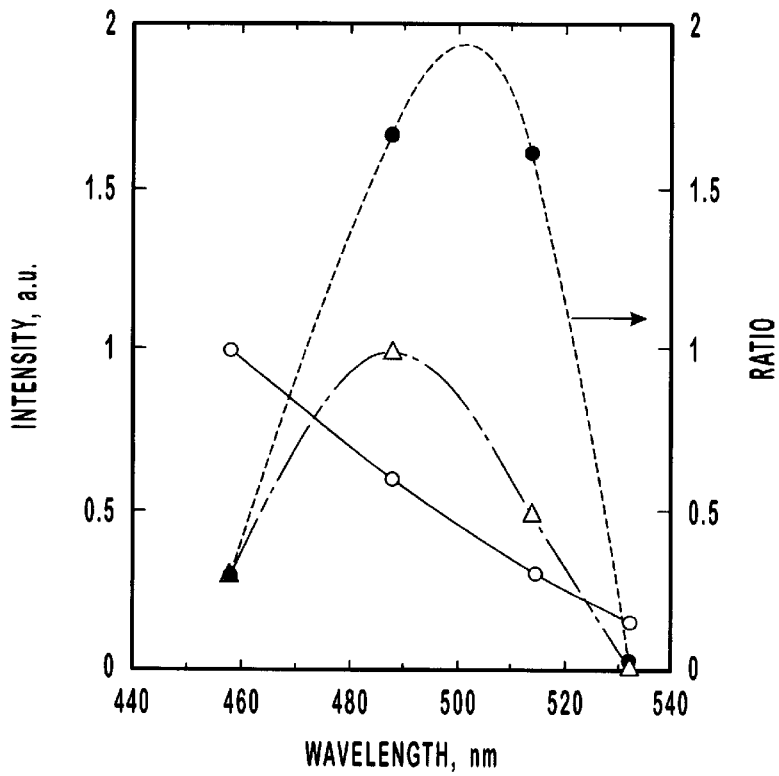
FIG. 7 is a graph showing the spectral dependencies of excitation efficiencies for Raman scattering of carotenoids and fluorescence of skin.

The Raman scattering intensity scales inversely with the fourth power of the excitation wavelength, which in practice, means that it strongly increases with shorter excitation wavelength. On the other hand, the overlapping fluorescence which masks the Raman signal, also increases with shorter wavelength. In the case of resonance Raman scattering, the light scattering efficiency is additionally influenced by the electronic absorption behavior of the scattering species, following in general the spectral dependence of the electronic absorption transition. Therefore, in order to find the optimum excitation conditions for maximum contrast between Raman peaks and fluorescence background, the excitation conditions were varied using five different argon laser lines and a frequency doubled Nd:YAG laser wavelength. The excitation power density was 0.2 W/cm$^2$, and the sampling time was 10 seconds. The results are given in the graph of FIG. 7, which shows the spectral dependencies for both the strongest Raman carotenoid peak intensity at 1520 cm$^{-1}$ (open triangles), and the background fluorescence of skin (open circles). From the ratio of Raman to fluorescence intensity, shown as solid dots in the graph of FIG. 7, an optimum excitation wavelength is seen to exist in the 500 nm wavelength region. The available strongest argon ion laser wavelengths of 4880 and 5145 Å are close to this optimum wavelength, and the required power levels can be easily achieved with a compact and relatively inexpensive air-cooled laser.

EXAMPLE 5

Figure 8:
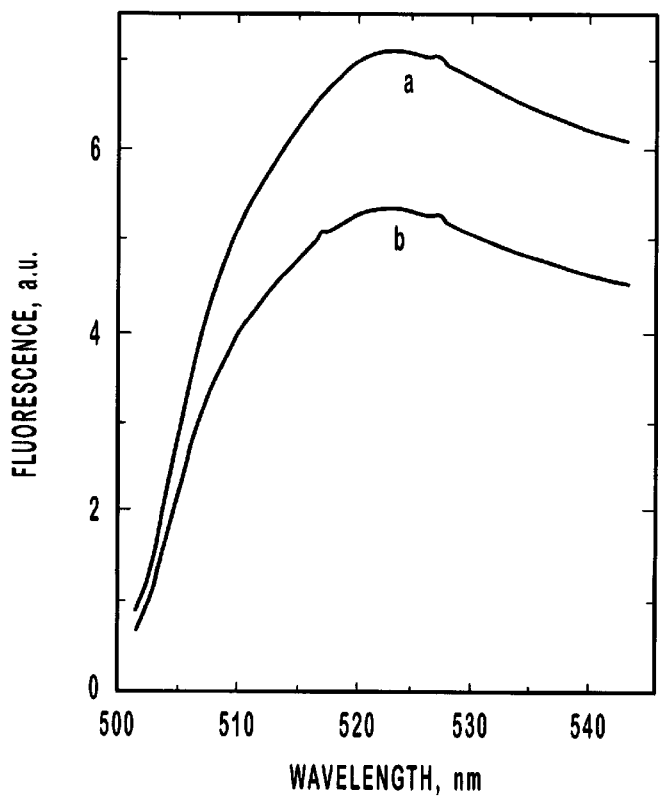
FIG. 8 is a graph showing the fluorescence spectra of skin with partial bleaching of the fluorescence.

In the course of performing Raman measurements, it was discovered that the fluorescence background of human skin bleached partially over a time period of several minutes. This effect is shown in the graph of FIG. 8, where curve (a) corresponds to the fluorescence background immediately after exposure of a "fresh" skin spot, and curve (b) corresponds to the fluorescence background after a 7 minute exposure with 488 nm argon laser light, using a (safe) power density of 200 mW/cm$^2$. While the shape of the fluorescence spectra remained unchanged, the intensity dropped to about 70% of its initial value. This value appears stable against further light exposure.

Figure 9:
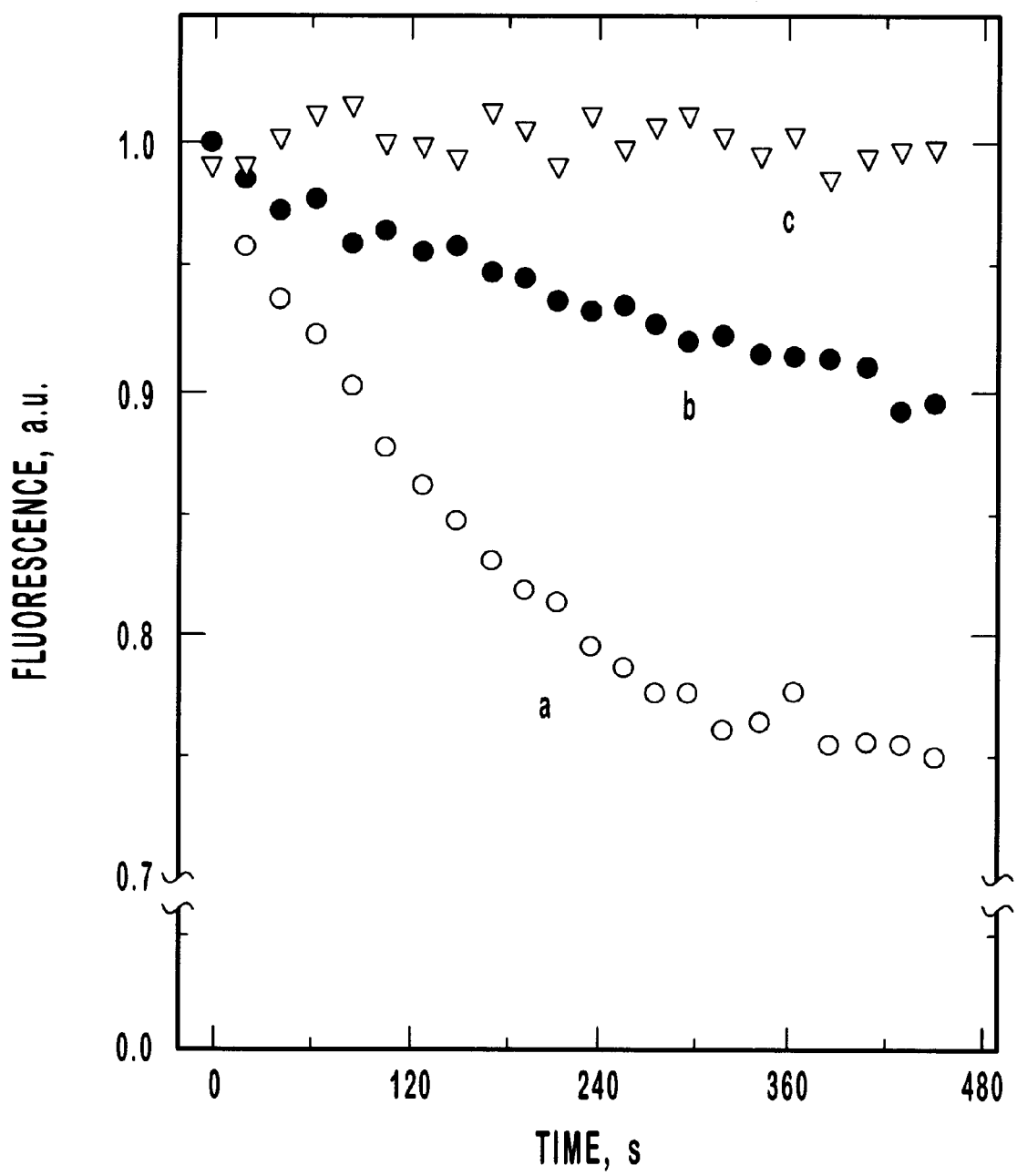
FIG. 9 is a graph showing the kinetics of the bleaching behavior of human skin fluorescence.

The kinetics of the bleaching behavior of human skin fluorescence was further investigated. The results are shown in the graph of FIG. 9, where the intensities of fluorescence at 525 nm versus time under irradiation with a 488 nm argon laser are plotted for the two excitation intensities, 200 mW/cm$^2$ (curve a) and 25 mW/cm$^2$ (curve b), respectively, showing that the fluorescence follows complicated non-exponential decay kinetics. Also shown in FIG. 9 is the intensity versus time of the 1524 cm$^{-1}$ carotenoid Raman peak (curve c), revealing that it remained substantially unchanged under the same power density level leading to fluorescence bleaching.

EXAMPLE 6

Figure 10:
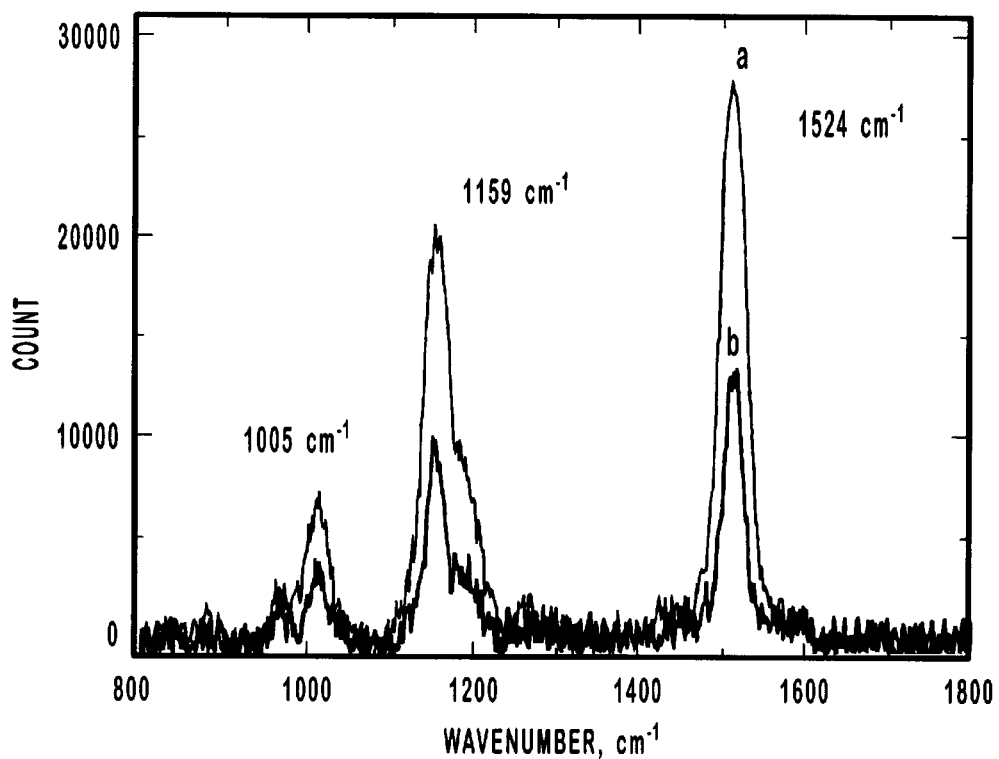
FIG. 10 is a graph showing the Raman spectra of living human skin measured at various locations.

The apparatus of Example 1 was used to measure the carotenoid content in various skin regions of the body of a healthy human volunteer. The graph of FIG. 10 shows the fluorescence subtracted Raman spectral results from measurements of a finger (curve a) and the forehead (curve b) of the volunteer. The Raman response from the finger and, correspondingly, the carotenoid concentration, is seen to be about twice as high as the response from the forehead, showing that different levels of carotenoids are present in various skin areas of the body.

Additional preliminary findings obtained from intact skin of volunteers indicate that carotenoid levels vary significantly from person to person, even in the same body area. For example, it was found that the carotenoid levels of two white male foreheads differed by a factor of 38. Further preliminary data suggest that carotenoid levels decrease especially in smokers.

EXAMPLE 7

Figure 11:
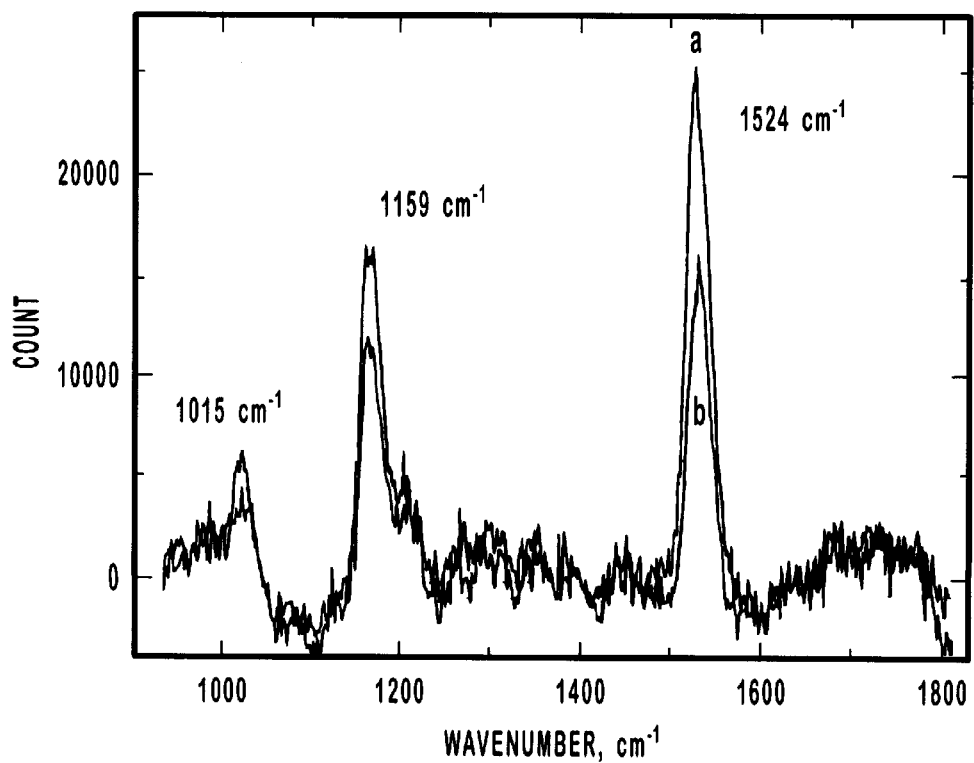
FIG. 11 is a graph showing the Raman spectra of healthy skin and an adjacent carcinomic area of skin.

The apparatus of Example 1 was used to measure the carotenoid content in skin regions of the body of a human volunteer suffering from squamous cell carcinoma. The graph of FIG. 11 shows the fluorescence subtracted Raman spectral results from measurements of a healthy skin region near the carcinoma (curve a), and the results from measurements of the central region of the carcinoma (curve b). The peaks associated with the carotenoids are measured at 1015 cm$^{-1}$, 1159 cm$^{-1}$ and 1524 cm$^{-1}$. The peak of curve (a) corresponds to a relatively high level of carotenoids in healthy skin, as indicated by the high photon count (intensity). The peak of curve (b) shows a much smaller photon count, indicating a lower level of carotenoids in carcinomic skin. Thus, a significant difference appears to exist in the carotenoid concentration of both regions, with the carcinoma area having a diminished carotenoid content.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for noninvasively determining the presence or risk of a malignancy disease in biological tissue, comprising the steps of:
   obtaining a light sourse which generates light at a wavelength that produces a Raman tenoids to be detected;
   directing light from the light sourse onto biological tissue for which carotenoid levels are to be measured, the light having an intensity which does not cause destruction of the tissue and does not substantially alter carotenoid levels in the tissue;
   collecting light scattered from the tissue, the scattered light including elastically and inelastically scattered light, the inelastically scattered light producing a Raman signal corresponding to carotenoid in the tissue;
   filtering out the elastically scattered light; and
   quantifying the intensity of the Raman signal, wherein a substantial difference between the intensity of the Raman signal and the intensity of Raman scattering from adjkacent normal biological tissue indicates the presence or risk of a malignancy disease.

2. The method of claim 1, wherein the light source generates light in a wavelength which overlaps the absorption bands of the carotenoids to be detected.

3. The method of claim 1, wherein the light source generates laser light in a wavelength range from about 450 nm to about 520 nm.

4. The method of claim 1, wherein the biological tissue resides in a live subject.

5. The method of claim 1, wherein the biological tissue is living skin.

6. The method of claim 5, wherein the light has an intensity of up to about 200 mW/cm$^2$.

7. The method of claim 5, wherein the scattered light is measured at frequencies characteristic of carotenoids in the skin.

8. The method of claim 1, wherein the Raman signal is quantified via signal intensity calibrated with actual carotenoid levels.

9. A method for noninvasively determining the antioxidant status in skin tissue, comprising the steps of:
obtaining a light source which generates light at a wavelength that produces a Raman response with a wavelength shift for carotenoids to be detected in skin tissue;
directing light from the light source onto skin tissue for which carotenoid levels are to be measured, the light having an intensity which does not cause destruction of the tissue and does not substantially alter carotenoid levels in the tissue;
collecting light scattered from the tissue, the scattered light including elastically and inelastically scattered light, the inelastically scattered light producing a Raman signal corresponding to carotenoids in the tissue;
filtering out the elastically scattered light; and
quantifying the intensity of the Raman signal in order to assess the antioxidant status of the tissue.

10. The method of claim 9, wherein the light source generates light in a wavelength which overlaps the absorption bands of the carotenoids to be detected.

11. The method of claim 9, wherein the light source generates laser light in a wavelength range from about 450 nm to about 520 nm.

12. The method of claim 9, wherein the skin tissue resides in a live subject.

13. The method of claim 9, wherein the skin tissue is living skin.

14. The method of claim 13, wherein the scattered light is measured at frequencies characteristic of carotenoids in the skin.

15. The method of claim 9, wherein the Raman signal is quantified via signal intensity calibrated with actual carotenoid levels.

16. A method for noninvasive measurement of carotenoids in skin tissue, comprising the steps of:
obtaining a light source which generates light at a wavelength that produces a Raman response with a wavelength shift for carotenoids to be detected;
directing light from the light source onto skin tissue for which carotenoid levels are to be measured, the light having an intensity which does not cause destruction of the skin tissue and does not substantially alter carotenoid levels in the skin tissue;
collecting light scattered from the skin tissue, the scattered light including elastically and inelastically scattered light, the inelastically scattered light producing a Raman signal corresponding to carotenoids in the skin tissue;
filtering out the elastically scattered light;
quantifying the intensity of the Raman signal; and
subtracting a background fluorescence signal of the skin tissue from the Raman signal of the carotenoids being detected.

17. The method of claim 16, wherein the light source generates light in a wavelength which overlaps the absorption bands of the carotenoids to be detected.

18. The method of claim 16, wherein the light source generates laser light in a wavelength range from about 450 nm to about 520 nm.

19. The method of claim 16, wherein the light has an intensity of up to about 200 mW/cm$^2$.

20. The method of claim 16, wherein the scattered light is measured at frequencies characteristic of carotenoids in the skin.

21. The method of claim 16, wherein the Raman signal is quantified via signal intensity calibrated with actual carotenoid levels.

22. An apparatus for noninvasive measurement of carotenoids and related chemical substances in biological tissue, comprising:
a laser light source that generates light at a wavelength giving a Raman response with a wavelength shift for carotenoids being detected;
a light delivery and collection module for directing light onto biological tissue and collecting scattered light from the tissue such that the light does not damage the tissue or substantially alter the carotenoid levels in the tissue, the light delivery and collection module comprising:
a first lens for collimating laser light;
a first narrow bandwidth filter in optical communication with the first lens;
first and second dichroic beam splitters in optical communication with the first narrow bandwidth filter;
a second lens adapted to direct a beam of laser light from the second dichroic beam splitter to tissue and collect scattered light from the tissue;
a second narrow bandwidth filter in optical communication with the second lens; and
a third lens in optical communication with the second narrow bandwidth filter;
a spectrally selective system for selecting Raman shifted light from the collected scattered light;
detection means for scanning and measuring the Raman shifted light at frequencies characteristic of carotenoids; and
quantifying means for determining Raman signal intensity for the carotenoids being detected.

23. The apparatus of claim 22, wherein the light source generates laser light in a wavelength range from about 450 nm to about 520 nm.

24. The apparatus of claim 22, wherein the spectrally selective system is a grating spectrometer.

25. The apparatus of claim 22, wherein the spectrally selective system includes a grating monochromator.

26. The apparatus of claim 22, wherein the spectrally selective system includes a holographic filter.

27. The apparatus of claim 22, wherein the spectrally selective system includes a dielectric filter.

28. The apparatus of claim 22, wherein the spectrally selective system includes an acousto-optic filter.

29. The apparatus of claim 22, wherein the detection means comprises a CCD detector array.

30. The apparatus of claim 22, wherein the detection means comprises an intensified CCD detector array.

31. The apparatus of claim 22, wherein the quantifying means comprises a personal computer.

32. The apparatus of claim 22, wherein the quantifying means comprises a CCD image display or monitor.

* * * * *

UNITED STATES PATENT AND TRADEMARK OFFICE
CERTIFICATE OF CORRECTION

PATENT NO. : 6,205,354 B1
DATED : March 20, 2001
INVENTOR(S) : Werner Gellermann et al.

It is certified that error appears in the above-identified patent and that said Letters Patent is hereby corrected as shown below:

Column 5,
Line 33, after "rotational" insert -- eigenstates associated with specific chemical structures, and hence provide a "fingerprint" --

Column 7,
Line 66, after "reflected" change "offofbeam" to -- off of beam --

Column 12,
Line 54, after "light" change "sourse" to -- source --
Line 55, after "Raman" delete "tenoids" and insert -- response with a wavelength shift for carotenoids --
Line 56, after "the light" change "sourse" to -- source --
Line 64, after "corresponding to" change "carotenoid" to -- carotenoids --

Column 13,
Line 2, before "normal" change "adjkacent" to -- adjacent --

Signed and Sealed this

Thirteenth Day of May, 2003

JAMES E. ROGAN
*Director of the United States Patent and Trademark Office*